United States Patent [19]

Boyce

[11] Patent Number: 4,797,956

[45] Date of Patent: Jan. 17, 1989

[54] EYE SHIELD

[75] Inventor: Elvin L. Boyce, Salt Lake City, Utah

[73] Assignee: Professional Tape Converters, Inc., Salt Lake City, Utah

[21] Appl. No.: 108,925

[22] Filed: Oct. 15, 1987

[51] Int. Cl.⁴ .............................................. A61F 9/02
[52] U.S. Cl. .............................................. 2/431; 2/9; 2/13; 128/858
[58] Field of Search ................ 2/9, 13, 206, 439, 454, 2/426, 174, 427, 431; 128/132 R, 139, 206.19, 163

[56] References Cited

U.S. PATENT DOCUMENTS

| 450,515 | 4/1891 | Lamb | 2/174 X |
|---|---|---|---|
| 1,923,340 | 8/1933 | Steckler | 2/174 |
| 1,932,326 | 10/1933 | Sievers | 2/174 |
| 2,081,779 | 5/1937 | Titus | 2/206 UX |
| 3,241,155 | 3/1966 | Phillips | 2/9 |
| 4,571,748 | 2/1986 | Carroll et al. | 2/439 X |
| 4,621,378 | 11/1986 | Hatchman | 2/9 |
| 4,688,566 | 8/1987 | Boyce | 128/206.19 |

FOREIGN PATENT DOCUMENTS 1017305  1/1966  United Kingdom ............... 2/174

Primary Examiner—Peter Nerbun
Attorney, Agent, or Firm—Workman, Nydegger & Jensen

[57] ABSTRACT

An eye shield adapted for use either singly or in combination with a protective face mask. The eye shield includes a flexible transparent material which is generally flat in shape. A moldable stiffener is attached to the bottom edge of the transparent material and permits the transparent material to be molded to conform to the wearers nose and cheeks. Means for spacing the transparent material away from the wearer's eyes is attached to the upper edge of the transparent material opposite the moldable stiffener. A single elastic head band, attached to the other two sides of the transparent material, draws the eye shield closely against the face. Whe used in combination with a protective face mask, the bottom edge of the eye shield overlaps the face mask and provides a shingling effect which keeps any harmful fluids or debris on the outer surfaces of the eye shield and face mask.

18 Claims, 2 Drawing Sheets

EYE SHIELD

BACKGROUND

1. Field of the Invention

The present invention relates to eye shields. More particularly, the present invention is directed to a eye shield adapted for use either singly or in combination with a protective face mask so as to provide effective eye protection from small objects and harmful or contaminated fluids which might otherwise contact the eyes.

2. The Prior Art

In recent years there has been increased interest in eye protection. This is particularly evident in the area of industrial safety. At many industrial sites personnel, including visitors, are required to wear eye protection when working or walking through certain areas. This concern for eye safety is becoming more prevalent throughout our society. For example, youth are taught the importance of eye protection in industrial art classes, science classes, and other courses where students engage in activities which involve potential harm to the eyes. Manufacturers of various consumer products often warn the purchaser of the need to wear eye protection during use of such products.

Thus, the need for eye protection is being recognized in more and more facets of our society. A current example of the need for eye protection in certain situations is illustrated by a recent report that certain medical care workers contracted Acquired Immune Deficiency Syndrome (AIDS) through contact with the eyes of contaminated fluid. Heretofore, there was no recognized need for eye protection as a preventive measure against AIDS.

When a medical or health care professional such as a doctor or dentist knows that a patient carries the AIDS virus, proper precaution can be taken to avoid contact with contaminated body fluids. However, the most serious risk facing medical and health care professionals is the person who is unknowingly carrying the AIDS virus. Thus, increasingly, persons in the health care industry are taking percautionary measures with all persons they treat.

Of the known eye protection devices in the art, none adequately serves the needs of today's medical professional who is exposed to the AIDS virus.

For example, safety glasses are a well-known and widely used form of eye protection. They are, however, rather costly to manufacture. Moreover, because safety glasses are bulky, special packaging is required to protect them from damage during shipment.

Goggles are another common form of eye protection. They may be worn over normal prescription glasses or directly over the eyes.

Goggles are also generally large and bulky making them relatively more expensive and more difficult to package and ship in quantity.

Another known eye protection device is a face shield or mask, such as typified by a welder's mask. The face shield usually has a portion of highly tinted glass to protect the wearer's eyes from the bright light involved in welding. Such a shield is very specialized and has little other practical use outside of welding.

In the health care field, it is particularly important that the eye shield be adapted for use in combination with a protective face mask. The eye shield should be able to be sterilized and stored in a sterile state. The eye shield should be able to adjust or confirm to the wearer's nose and cheeks such that no harmful fluids or debris can come in contact with the eyes. Furthermore, it is very important that the eye shield overlap the protective face mask, thereby providing a "shingling effect." Thus, if any harmful fluids or debris strike the eye shield, they will simply roll down the eye shield and remain on the outside of the face mask. In this way, the mouth and nose are also protected.

In addition, for some uses an eye shield should be disposable. The term "disposable" generally means that the cost of the eye shield is such that it may be disposed of after only a single use. Generally, the vast majority of eye shields used in industrial, academic, or domestic applications are nondisposable. There are many applications where eye protection is needed for only a single occurrence, or where a low-cost disposable eye shield is preferred.

BRIEF SUMMARY AND OBJECTS OF THE INVENTION

The present invention is directed to an eye shield adapted for use either singly or in combination with a protective face mask. The eye shield includes a flexible transparent material which is generally rectangular in shape. A moldable stiffener is attached to the bottom edge of the transparent material. This moldable stiffener permits the transparent material to be molded to conform to the wearer's nose and cheeks.

Means for spacing the transparent material away from the wearer's eyes is attached to the upper edge of the transparent material opposite the moldable stiffener. In one embodiment of the present invention, a reverse fold provides the desired spacing. The reverse fold consists of a portion of the transparent material folded inwardly towards the wearer's face and down against the transparent material. A moldable stiffener may optionally be attached to the upper edge of the transparent material which was folded down to provide for adjustable spacing.

In another embodiment of the present invention a foam filler is inserted within the space created by a reverse fold to provide spacing between the eye shield and the eyes.

In yet another embodiment, a foam strip is attached to the upper edge of the transparent material to maintain the desired spacing between the eye shield and the eyes.

A single elastic headband is attached to the other two sides of the transparent material. The elastic headband draws the eye shield closely against the face, gently maintaining the eye shield in position.

When used in combination with a protective face mask, the bottom edge of the eye shield overlaps the face mask and provides a shingling effect by keeping any harmful fluids or debris on the outer surfaces of the eye shield and face mask.

The eye shield may be economically manufactured. Furthermore, when not in use, the eye shield has a flat configuration permitting simple packaging and easy shipment.

It is, therefore, an object of the present invention to provide an eye shield adapted for use either singly or in combination with a protective face mask, and which may be stored in a flat configuration, does not require complex packaging, and cannot be damaged during shipping.

Another important object of the present invention is to provide an eye shield which may be easily manufactured and is inexpensive enough to be disposed of after a single use.

An additional important object of the present invention is to provide an eye shield which may be conformed when installed on a wearer's face so as to produce a shingling effect when used in combination with a protective face mask.

Still another object of the present invention is to provide an eye shield which may be sterilized and stored in a sterile state.

A further important object of the present invention is to provide an eye shield adapted for use in combination with a protective face mask which is small and compact, yet will protect the wearer's eyes from harmful or contaminated fluids and/or flying debris.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

DETAIL DESCRIPTION OF THE PREFERRED EMBODIMENTS

Figure 1:
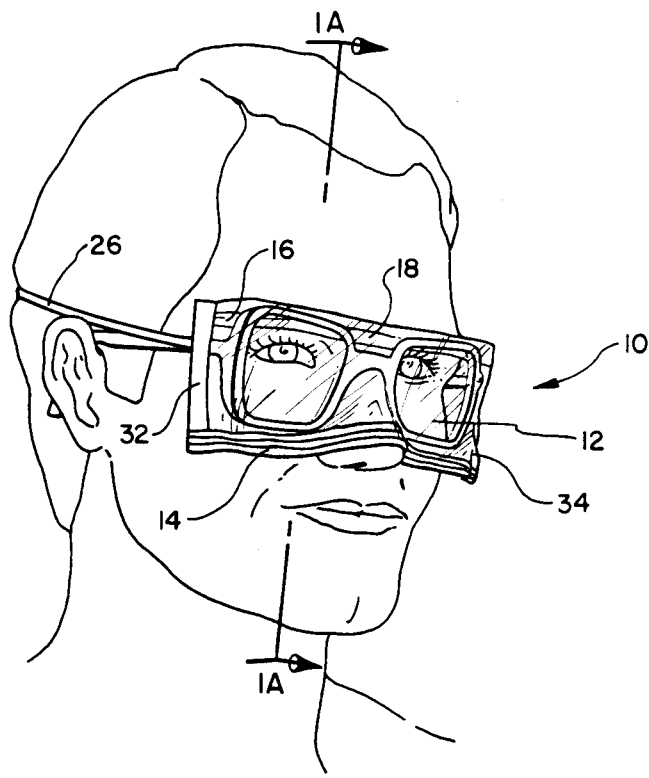
FIG. 1 is a perspective view of one presently preferred embodiment of the present invention shown installed on the face of a wearer.
Figures 1A, 2A, 3A:
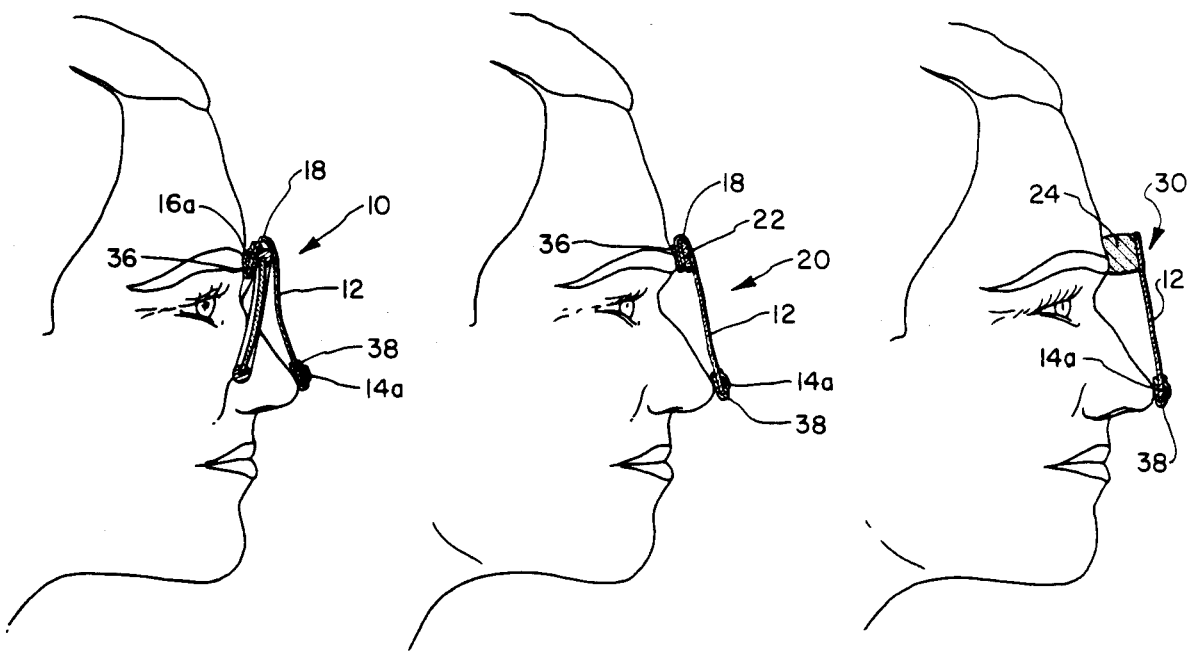
FIG. 1A is a cross-sectional view of FIG. 1 taken along line 1A—1A of FIG. 1.
FIG. 2A is a cross-sectional view of FIG. 2 taken along line 2A—2A of FIG. 2.
FIG. 3A is a cross-sectional view of FIG. 3 taken along line 3A—3A of FIG. 3.

Reference is now made to the drawings wherein like parts are designated with like numerals throughout. Referring first to FIGS. 1 and 1A, one presently preferred embodiment of the apparatus of the present invention is illustrated and generally designated 10.

Eye shield 10 includes a thin, flat, flexible transparent material 12 which is generally rectangular in configuration having at one edge a moldable stiffener means 14 comprised of a metal strip encased in heat-activated tape, as more fully explained below. At the opposite parallel edge a reverse fold 18 and another moldable stiffener means 16 are provided. A single elastic headband 26 is attached to two lateral edges 32 and 34. Moldable stiffeners 14 and 16 are encapsulated within heat activated tape 38 and 36 respectively.

The flexible transparent material 12 should be clear and should not interfere with vision. In addition, the flexible transparent material should possess inherent directional stability so as to be self-supportive. It should not be so pliant that a support frame is necessary to maintain its shape. The flexible transparent material may be constructed out of acetate, cellulose acetate butyrate, or any other suitable material known in the art. The flexible, transparent material may also be tinted to provide eye protection from bright light or the infrared or ultraviolet wavelengths.

The upper edge of the flexible transparent material comprises a means for spacing the eye shield away from the wearer's eyes. In the embodiment illustrated in FIG. 1, this is accomplished through a reverse fold 18 and a moldable stiffener 16. The reverse fold 18 is formed by folding a portion of the flexible transparent material towards the inner surface of the flexible transparent material 12. A moldable stiffener 16 is secured to the edge of the flexible transparent material that is folded down.

If the user is wearing eye glasses, then the reverse fold 18 may fit behind the top of the eyeglasses and assist in keeping the eye shield in place. This feature is illustrated in FIGS. 1 and 1A.

It should be understood that the use of the term "moldable stiffener" herein is meant to include the use of both moldable and flexible stiffeners. It is preferred that moldable stiffener 16 be placed directly next to the upper edge of flexible transparent material 12. An important property of the moldable stiffener 16 is that it is pliant enough to be bent to a shape that conforms to the face of the wearer, and retains heat shape. In this regard, it is important that moldable stiffener 16 not be too stiff so as to make if difficult for the wearer to conform the mask upon installation. Moldable stiffener 16 also provides a means for adjusting and helping to maintain desired spacing between the reverse fold 18 and the flexible transparent material 12.

A moldable stiffener 14 is also secured to the lower portion of the flexible transparent material. Moldable stiffener 14 is designed to be bent to a shape that conforms to the nose and cheeks of the wearer. In this way, a single eye shield size may be adapted to fit virtually any wearer.

While several different methods of attaching the moldable stiffeners 14 and 16 to the flexible transparent material 12 are available, one presently preferred method is that of encapsulating the stiffeners within heat-activated tape which becomes adhesive when it is heated. Such heat-activated tape is well-known in the art and is commercially available. Encapsulating the moldable stiffeners within a binding of heat-activating tape provides a convenient structure for holding the moldable stiffeners 14 and 16 in place.

Any edges of the flexible transparent material, rather than being left unfinished, are also preferably bound by heat-activated tape. For example, lateral edges 32 and 34 are bound by heat-activated tape.

In the present invention, an elastic headband 26 is the present preferred method of securing the eye shield 10 in the proper position on the face. Use of elastic headband 26 allows the eye shield to be easily installed on the wearer and avoids the difficulty of tying a string behind the head. Furthermore, since headband 26 is elastic, there is not the risk of the headband becoming untied at an inopportune moment. In addition, the elasticity of the headband material may be chosen so as to allow eye shield 10 to be easily repositioned on the face while only using one hand.

The characteristics of elastic headband 26 which are of concern to the present invention are its length, width, and extensibility. The length of elastic headband 26 must be chosen so as to provide force to properly hold the eye shield on the face of the smallest wearer contemplated. However, elastic headband 26 must be long enough so that excessive pressure is not exerted upon the head of the wearer.

The comfort of eye shield 10 can be greatly increased by choosing headband 26 of proper width. If headband 26 is of proper width, the force against the wearer's head will be distributed over a greater surface area than if a narrower headband 26 were used.

Also, since the length of headband 26 may be limited due to practical considerations, the extensibility of headband 26 may be altered to fit the particular circumstances. Thus, the comfort of the wearer may be greatly increased by using a headband of proper length, width, and extensibility. Many materials which are available in the art suitable for use as elastic headband 26.

It will be appreciated that other band means may be used to secure the eye shield in place. For instance, a single or double tie configuration could be used instead of an elastic headband.

Figure 2:
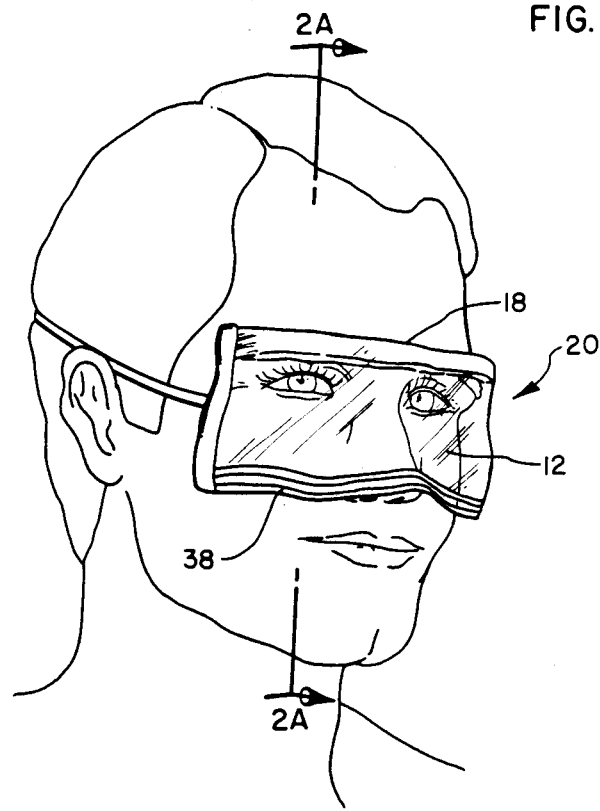
FIG. 2 is a perspective view of another preferred embodiment of the present invention in use.
Figure 3:
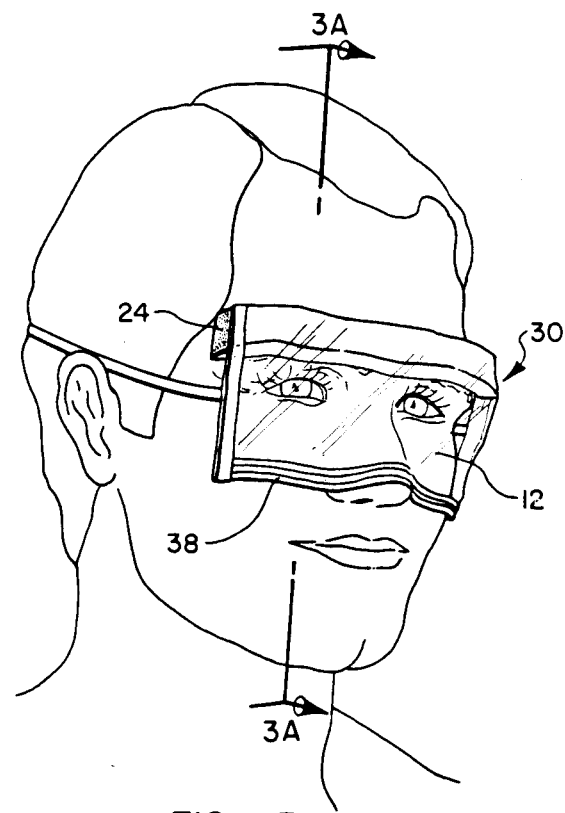
FIG. 3 is a perspective view of yet another preferred embodiment of the present invention in use.

Importantly, as shown best in FIGS. 1-3, the eye shield 10 has a generally flat configuration. Thus, prior to being installed on a wearer the eye shield may be compactly stored. This greatly facilitates a more simple, economical manufacturing process and also accommodates packaging and shipping in large quantities.

A second preferred embodiment of the present invention, generally designated 20, is illustrated in FIGS. 2 and 2A. Eye shield 20 is structurally identical to eye shield 10 except that the means for spacing the eye shield 20 for the wearer's eyes comprises foam filler 22 rather than moldable stiffener 16. Foam filler 22 is placed between reverse fold 18 and the flexible transparent material 12. Foam filler 22 assures the desired spacing between the eye shield and the wearer's eyes. Many materials which are available in the art are suitable for use as foam filler 22.

Another preferred embodiment of the present invention generally designated 30, is illustrated in FIGS. 3 and 3A. Eye shield 30 is structurally identical to eye shield 10 except that moldable stiffener 16 and reverse fold 18 of eye shield 10 are replaced by a foam strip 24 of eye shield 30. Foam strip 24 serves the same purpose as moldable stiffener 16 and reverse fold 18 by providing the desired spacing means for holding the eye shield away from the wearer's eyes a comfortable distance. Many materials which are available in the art are suitable for use as foam strip 24.

FIG. 1A is a cross-sectional view of the embodiment of the present invention illustrated in FIG. 1. FIG. 1A clearly illustrates the reverse fold 18 which provides spacing between the eye shield and the wearer's eyes. In addition, FIG. 1A clearly illustrates heat-activated tape 36 and 38 which surround the metal strips 16a and 14a respectively.

FIG. 2A is a cross-sectional view of the embodiment of the present invention illustrated in FIG. 2. Foam filler 22 is attached to both the inside surface of the reverse fold 18 and the flexible transparent material 12.

FIG. 3A is a cross-sectional view of the embodiment of the present invention illustrated in FIG. 3. Foam strip 24 is attached to the inside surface of flexible transparent material 12. As illustrated, foam strip 24 has a rectangular cross-section. It will be appreciated, however, that other cross-sectional configurations are possible within the scope of the present invention. What is important is that the foam strip 24 be securely attached to the flexible transparent material 12 and that foam strip 24 provide the desired spacing between flexible transparent material 12 and the wearer's eyes.

Figure 4:
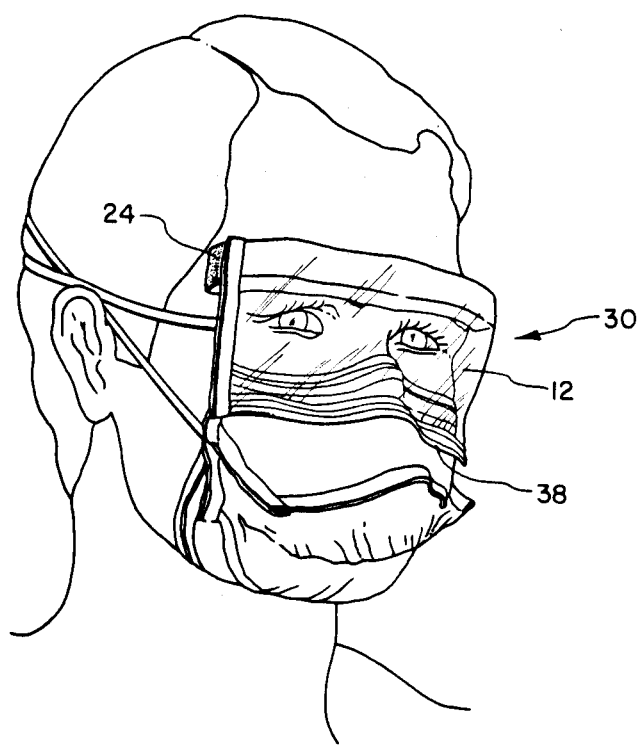
FIG. 4 is a perspective view of one presently preferred embodiment of the present invention illustrating its compatible use with a face mask.

FIG. 4 is a perspective view of one embodiment of the present invention used in conjunction with a face mask. The present invention is ideally suited for use with face masks such as those described in U.S. Pat. No. 4,688,566. When used in conjunction with the face mask, the present invention performs a unique shingling effect. If any harmful fluid or debris comes in contact with the eye shield, it will simple roll down the outside of the eye shield and on the outside of the face mask. The shingling effect prevents any such fluid or debris from getting inside the face mask and contaminating the wearer.

From the foregoing, it will be appreciated that the present invention provides an eye shield which is small and compact and will protect the wearer's eyes from harmful or contaminated fluids and/or flying debris.

Additionally, it will be appreciated that the present invention further provides an eye shield which is comfortable to wear and may be adjusted to fit each individual wearer through the use of the moldable stiffeners.

Likewise, it will be appreciated that the present invention also provides an eye shield which is simple to construct and may be manufactured economically enough to permit disposal after a single use.

It will also be appreciated that the present invention provides an eye shield which is compatible for use with face masks, providing a beneficial effect therewith, and may be packaged and provided in a sterilized condition if necessary.

It will also be appreciated that the present invention provides an eye shields which may be stored in a flat configuration and will not be damaged during shipping.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An eye shield comprising:
   a transparent medium having an inner surface to be worn near the wearer's eyes, an outer surface, a bottom portion, and a top portion;
   a reverse fold attached to said top portion and formed by folding said top portion towards said inner surface, said reverse fold serving to space the transparent medium away from the wearer's face such that the inner surface does not touch the wearers' eyes;
   a foam strip placed within said reverse fold so as to maintain the spacing between said inner surface and the wearer's eyes; and
   single band means for securing said eye shield to the head of the wearer.

2. An eye shield as defined in claim 1 further comprising first moldable stiffening means for conforming said transparent medium to the nose and cheek area of the wearer's face, said first moldable stiffening means being attached to said transparent medium along the bottom portion thereof.

3. An eye shield as defined in claim 3, wherein said reverse fold comprises moldable stiffening means for adjustably spacing the transparent medium away from the wearer's face.

4. An eye shield as defined in claim 1, wherein said means for spacing the transparent medium away from the wearer's face comprises a foam strip along the inner surface of the top portion of the transparent medium.

5. An eye shield as defined in claim 1, wherein said mean for securing said eye shield comprises a single elastic headband.

6. An eye shield for protecting a wearer's eyes against contamination from fluids or injury from objects, comprising:
   an essentially flat, flexible transparent medium having an inner surface to be worn near the wearer's eyes, an outer surface, a bottom portion, and a top portion;
   means for spacing the transparent medium away from the wearer's face such that the inner surface does not touch the wearer's eyes, said means for spacing being attached to said top portion;
   first moldable stiffening means for conforming said transparent medium to the wearer's nose and cheeks and attached to said transparent medium along said bottom portion, said first moldable stiffening means being laterally disposed and bendable across the wearer's nose and cheeks when the eye shield is installed upon the wearer's face so as to transform the transparent medium from an essentially flat configuration to one which conforms to the contour of the wearer's nose and cheeks; and
   single band means for securing said eye shield to the wearer's head.

7. An eye shield as defined in claim 6, wherein said means or spacing the transparent medium away from the wearer's face comprises a reverse fold formed by folding said top portion of said transparent medium towards said inner surface.

8. An eye shield as defined in claim 7, wherein said reverse fold comprises moldable stiffening means for adjustably spacing the transparent medium away from the wearer's face.

9. An eye shield as defined in claim 7, wherein said reverse fold comprises a foam strip placed within said reverse fold such that said foam strip serves to maintain spacing between said inner surface and the wearer's eyes.

10. An eye shield as defined in claim 6, wherein said means for spacing the transparent medium away from the wearer's face comprises a foam strip along the inner surface of the top portion of the transparent medium.

11. An eye shield as defined in claim 6, wherein said means for securing said eye shield comprises a single elastic headband.

12. An eye shield adapted for use in combination with a protective face mask so as to protect against combination from fluids or injury from objects, comprising:
   a generally flat, thin, flexible, transparent medium having an inner surface to be worn near the wearer's eyes, an outer surface, a bottom edge and a top edge, said transparent medium being sufficiently long such that said bottom edge overlaps the protective face mask;
   means for spacing the transparent medium away from the wearer's face such that the inner surface does not touch the wearer's eyes, said means for spacing being attached to said top edge;
   first moldable stiffening means for conforming said transparent medium to the wearer's nose and cheeks, said first moldable stiffening means being attached to said transparent medium along said bottom edge and being laterally disposed and bendable across the wearer's nose and cheeks when the eye shield is installed upon the wearer's head such that said bottom edge overlaps the protective face mask and transforms the transparent medium from an essentially flat configuration to one which conforms to the contour of the wearer's nose and cheeks, thereby providing a shingling effect which the protective face mask; and
   single band means for securing the eye shield to the wearer's head.

13. An eye shield as defined in claim 12, wherein said means for spacing the transparent medium away from the wearer's face comprises a reverse fold formed by folding said top portion of said transparent medium towards said inner surface.

14. An eye shield as defined in claim 13, wherein said reverse fold comprises moldable stiffening means for adjustably spacing the transparent medium away from the wearer's face.

15. An eye shield as defined in claim 13, wherein said reverse fold comprises a foam strip placed inside said reverse fold such that said foam strip serves to maintain spacing between the inner surface and the wearer's eyes.

16. An eye shield as defined in claim 12, wherein said means for spacing the transparent medium away from the wearer's face comprises a foam strip along the inner surface of the top portion of the transparent medium.

17. An eye shield as defined in claim 12, wherein said means for securing said eye shield comprises a single elastic headband.

18. An eye shield for protecting a wearer's eyes against contamination from fluids or injury from objects, comprising:
   a flexible transparent medium having a top portion, a bottom portion, two side edges, an inner surface to be worn near the wearer's eyes, and an outer surface;
   means for spacing the transparent medium away from the wearer's face such that the inner surface does not touch the wearer's eyes, said means for spacing being attached to said top portion;
   a first moldable stiffener attached to said transparent medium along said bottom portion, said moldable stiffener being laterally disposed and bendable across the wearer's nose and cheeks when the eye shield is installed upon the wearer's face so as to aid in conforming said transparent medium to the contour of the wearer's nose and cheeks;
   a second moldable stiffener laterally disposed at the upper portion of said transparent medium; and
   a single headband attached to the two side edges and in proximity to the top portion of said transparent medium, said headband being capable of partially encircling the wearer's head and thereby holding the eye shield securely installed on the wearer's head.

* * * * *

UNITED STATES PATENT AND TRADEMARK OFFICE
CERTIFICATE OF CORRECTION

PATENT NO.  :  4,797,956

DATED       :  January 17, 1989

INVENTOR(S) :  Elvin L. Boyce

It is certified that error appears in the above-identified patent and that said Letters Patent is hereby corrected as shown below:

```
Abstract, line 7, "wearers nose" should be --wearer's nose--
Abstract line 12, "Whe" should be --When--
Column 1, line 43, "percautionary" should be --precautionary--
Column 4, line 53, "present" should be --presently--
Column 6, lines 52-53, "wearers' eyes" should be --wearer's
eyes--
```

Signed and Sealed this

Fifth Day of December, 1989

Attest:

JEFFREY M. SAMUELS

Attesting Officer     Acting Commissioner of Patents and Trademarks